United States Patent

Erikson et al.

[11] 4,187,380
[45] Feb. 5, 1980

[54] ESTERS OF IMIDAZOLIDINEDIONE-BASED TRIEPOXIDES

[75] Inventors: J. Alden Erikson, Gibsonia; Ronald J. Lewarchik, Natrona Heights; William J. Birkmeyer, Oakmont, all of Pa.

[73] Assignee: PPG Industries, Inc., Pittsburgh, Pa.

[21] Appl. No.: 950,097

[22] Filed: Oct. 10, 1978

[51] Int. Cl.² ........................................... C07D 233/72
[52] U.S. Cl. ..................................... 548/310; 528/45; 528/73
[58] Field of Search ......................................... 548/310

[56] References Cited

U.S. PATENT DOCUMENTS

| | | | |
|---|---|---|---|
| 3,496,122 | 2/1970 | Niklaus et al. | 260/37 EP |
| 3,808,226 | 4/1974 | Habermeier et al. | 548/310 |
| 3,821,243 | 6/1974 | Habermeier et al. | 548/310 |
| 3,904,644 | 9/1975 | Jaeoer | 548/310 |
| 3,963,667 | 6/1976 | Schreiber et al. | 260/37 EP |

*Primary Examiner*—Natalie Trousof
*Attorney, Agent, or Firm*—Charles R. Wilson

[57] ABSTRACT

Esters of imidazolidinedione-based triepoxides are especially useful in coating compositions having a low organic solvent content. The esters have the formula:

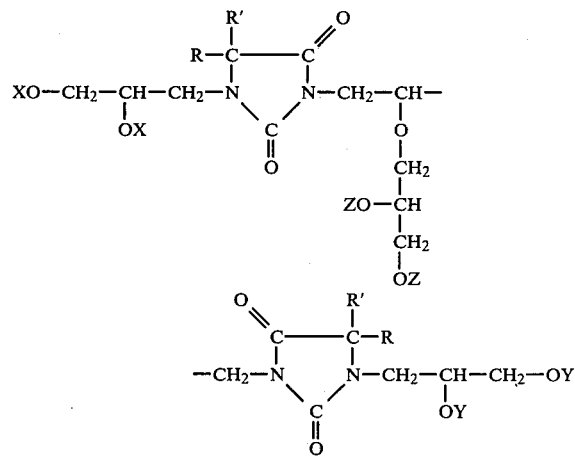

wherein R and R' are independently hydrogen or hydrocarbon groups having from 1 to 8 carbon atoms, one X is hydrogen, one Y is hydrogen, one Z is hydrogen and the other X, Y and Z are

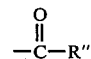

where the R" groups are independently hydrocarbon groups having from 1 to 17 carbon atoms.

10 Claims, No Drawings

ESTERS OF IMIDAZOLIDINEDIONE-BASED TRIEPOXIDES

BACKGROUND OF THE INVENTION

The subject invention reletes to novel esters and coating compositions containing them. More particularly, it relates to esters of imidazolidinedione-based triepoxides and their use in coating compositions.

There have been recent concerns as to the polluting effects and health concerns associated with the use of organic solvents. Many useful coating compositions contain appreciable amounts of organic solvents. Precaustions in the use of the coating compositions and the installation of solvent recovery systems have alleviated some of the concerns. However, it would still be desirable to formulate coating compositions containing little or no organic solvent.

Various attempts have been made to lower the organic solvent content is coating compositions. One line of work has concentrated on using water as the liquid carrier in place of the organic solvent. However, this has necessitated changes in the resin formulations with a consequent change in performance obtained from the coating compositions.

Another line of work has attempted to formulate coating compositions containing a high solids content, and thus low organic solvent content. The problem associated with many of the high solids coating compositions has been the fact such compositions normally are highly viscous and are hard to apply using conventional coating techniques. The formulation of coating compositions having a low organic solvent content which also possess a viscosity which allows the compositions to be applied by conventional techniques would be most desirable.

There have now been found novel compounds which when properly formulated into coating compositions provide compositions which can be readily applied and give coatings having a desired set of properties.

As used herein, all percents and ratios are by weight unless otherwise indicated.

SUMMARY OF THE INVENTION

The esters described herein have the formula:

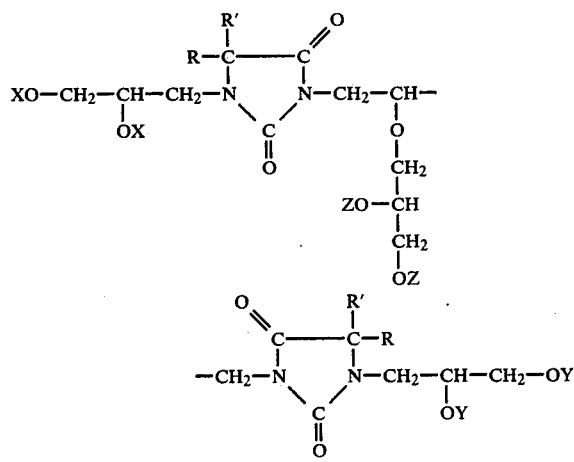

wherein R and R' are independently hydrogen or hydrocarbon groups having from 1 to 8 carbon atoms, one X is hydrogen, one Y is hydrogen, one Z is hydrogen and the other X, Y and Z are

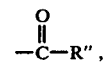

where the R" groups are independently hydrocarbon groups having from 1 to 17 carbon atoms.

The above esters of imidazolidinedione-based triepoxides are especially useful when formulated with a crosslinking agent selected from the group consisting of aminoplasts, isocyanates, blocked isocyanates, phenoplasts and mixtures thereof to form a coating compositions. The coating compositions can have an organic solvent content of below about 40 percent.

DETAILED DESCRIPTION OF THE INVENTION

The following paragraphs describe the esters of imidazolidinedione-based triepoxides, their process of making and their use in coating compositions.

Esters of imidazolidinedione-based triepoxides of this invention have the formula:

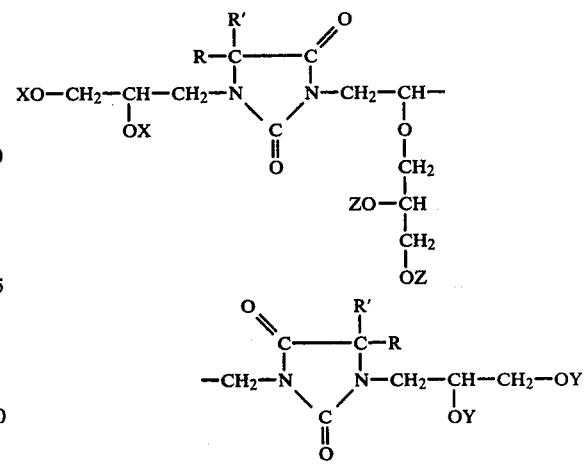

wherein R and R' are independently hydrogen or hydrocarbon groups having from 1 to 8 carbon atoms, one X is hydrogen, one Y is hydrogen, one Z is hydrogen and the other X, Y and Z are

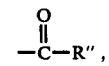

where the R" groups are independently hydrocarbon groups having from 1 to 17 carbon atoms.

The above-described esters are made by the reaction of triglycidyl compounds having the formula:

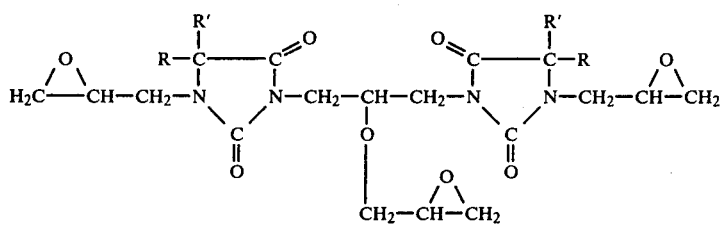

with a monocarboxylic acid. R and R' represent hydrogen groups, alkyl groups or, when joined together, a cycloalkyl group. (It should be understood that the R and R' groups can be the same or different.) Preferably, R and R' are alkyl groups having from 1 to 5 carbon atoms. The triglycidyl compounds are commercially available. U.S. Pat. No. 3,963,667, the disclosure of which is herein incorporated by reference, describes the compounds. The monocarboxylic acids can be saturated or unsaturated, aliphatic or cyclic compounds. The saturated aliphatic carboxylic acids have from 2 to 18 carbon atoms. Cyclic carboxylic acids used in the reaction are aryl and alkylaryl compounds having from 7 to 11 carbon atoms, i.e., 6 to 10 carbon atoms exclusive of the carbon atom in the carboxyl group. Examples of such acids include acetic acid, propionic acid, butyric acid, caproic acid, myristic acid, palmitic acid, stearic acid, neodecanoic acid, dodecanoic acid, pelargonic acid, benzoic acid, toluic acid and phenylactic acid. Unsaturated carboxylic acids can also be used. Such acids contain from 3 to 18 carbon atoms, preferably from 5 to 18 carbon atoms, examples of which are myristoleic acid, palmitoleic acid, oleic acid, linoleic acid and linolenic acid. The saturated carboxylic acids are preferred with the saturated carboxylic acids having from 8 to 18 carbon atoms being most preferred. A particularly preferred saturated carboxylic acid is neodecanoic acid.

The formation of the ester occurs at a temperature of from about 50° C. to about 200° C. A suitable catalyst such as a tertiary amine, quaternary ammonium hydroxide, quarternary ammonium halide or lithium carbonate can be used.

The above-described esters have a relatively low molecular weight, yet at substantially non-volatile upon exposure to elevated temperatures. The esters can be thinned with a small amount of solvent to substantially reduce their viscosities. These properties make the esters especially useful in coating compositions where only a low level of organic solvent can be tolerated. Thus coating compositions can be formulated with the esters and suitable crosslinking agents using little or no organic solvent. The resultant compositions have a low viscosity and can be applied using conventional coating techniques. Moreover, coatings resulting from the compositions are durable, have a good appearance and can have a high gloss.

COATING COMPOSITIONS

Coating compositions of this invention consist essentially of from about 5 percent to about 90 percent of the above ester of imidazolidinedione-based triepoxide, preferably from about 10 percent to about 50 percent of the ester, and from about 5 percent to about 80 percent, preferably from about 20 percent to about 60 percent, of a suitable crosslinking agent. Examples of crosslinking agents are the aminoplasts, isocyanates, blocked isocyanates, phenoplasts and mixtures thereof. Preferred are the aminoplasts and blocked isocyanates. The aforedescribed classes of crosslinking agents are described in more detail in the following paragraphs.

Aminoplast resins are based on the addition products of formaldehyde, with an amino- or amido-group carrying substance, e.g., urea, ethylene diurea, ethylene urea, melamine and benzoguanamine. Condensation products obtained from the reaction of alcohols and formaldehyde with melamine, urea or benzoguanamine are preferred herein. Useful alcohols used to make etherified products are monohydric alcohols such as methanol, ethanol, propanol, butanol, benzyl alcohol and butoxyethanol. An etherified melamineformaldehyde resin is the preferred aminoplast resin. U.S. Pat. No. 4,075,141, Porter et al. Feb. 21, 1978 contains a description of useful aminoplast resins and is incorporated herein by reference.

Isocyanates useful as a crosslinking agent include any of the many organic isocyanates available. Examples include p-phenylene diisocyanate, biphenyl diisocyanate, toluene diisocyanate, 3,3'-dimethyl-4, 4'-biphenylene diisocyanate, 1,4-tetramethylene diisocyanate, hexamethylene diisocyanate, 2,2,4-trimethylhexane-1,6-diisocyanate, methylene bis-(phenyl-isocyanate), isophorone diisocyanate, 1,2,4-benzene triisocyanate, polymethylene polyphenyl isocyanate, bis-(isocyanatocyclohexyl)methane and methyl cyclohexyl diisocyanate, as well as derivatives thereof.

Blocked isocyanates containing sustantially no free isocyanate groups and relatively inactive at room temperature are very useful cross-linking agents. Typical blocking agents are the phenols, thiols, oximes, caprolactams, and secondary aromatic amines. Many of these compounds are commercially available. "The Chemistry of Organic Film Formers", Robert E. Krieger Pub. Co., copyrighted 1977, by D. H. Solomon pp. 216–217, contains a description of many blocked isocyanates that can be used here. The disclosure of this publication is herein incorporated by referernce.

Phenoplast resins include the condensation product of an aldehyde with a phenol. Formaldehyde is preferred aldehyde. Various phenols can be used, e.g., phenol per se, cresol, para-phenylphenol, para-tertiaryphenol, para-tertiaryamylphenol and cyclopentylphenol. The methylol phenol ethers described in U.S. Pat. No. 2,597,330 (herein incorporated by reference) are especially useful.

The coating compositions consist essentially of the aforedescribed ester of imidazolidinedione-based triepoxides and the cross-linking agents. Generally, however, coating composition additives are included in the compositions. A solvent such as water or an organic solvent, e.g., the ketones, ethylene glycol monoalkyl ether acetates, the mono- and dialkyl ethers of ethylene and propylene glycol, xylene, toluene and lower alcohols can be used. The level of the organic solvent in the composition, however, is less than about 40 percent, preferably less than about 30 precent, of the composition. Other coating composition additives include pigments, fillers, antioxidants, flow control agents, surfactants, catalysts and reactive diluents. Other curable resins can also be included in the coating compositions provided such resins do not exceed about 60 percent of the composition.

The coating compositions are applied by any convenient method, including spraying, dipping and flow coating. The compositions have been found espcially useful for the coating of metal substrates such as automotive parts.

The following examples are illustrative of the described invention. The described processes all produce the esters of imidazolidinedione-based triepoxides of this invention.

EXAMPLE I

A three-liter reaction flask is equipped with heating means, stirring means and a nitrogen blanket. The flask is initially charged with 1,000 grams of 3,3'-(2-glycidyloxy-propylene)-bis-(1-glycidyl-5,5-dimethyl-2,4-imidazolidinedione, available from the Ciba-Geigy Co. as XB-2818, 868 grams of pelargonic acid and 5.6 grams of dimethyl-coco-amino The reaction mixture is heated to 120° C. and allowed to exotherm to about 140° C. The mixture is kept at 140° C. for about 3 hours until an acid number below 1 is obtained. After this reaction period, the product is thinned to 84 percent solids with 330 grams of ethylene glycol monoethyl ether acetate. The resultant mixture has a Gardner-Holdt viscosity of Y, and a hydroxyl number of 162.8.

EXAMPLE II

A three-liter reaction flask set up as in EXAMPLE I is charged with 972 grams of 3,3'-(2-glycidyloxy-propylene)-bis-(1-glycidyl-5,5-dimethyl-2,4-imidazolidinedione, 1050 grams neodecanoic acid and 6.1 grams dimethyl-coco-amine. The mixture is heated to 120° C. and then allowed to exotherm to 140° C. The mixture is held at 140° C. until an acid number of 3.3 is obtained. The reaction mixture is now thinned with 337 grams of ethylene glycol monoethyl ether acetate. The resultant product has a viscosity of Z-4 and acid number of 1.8.

EXAMPLE III

A coating composition is formulated as follows:

|  | Percent |
| --- | --- |
| Ester of Example I | 36.3 |
| Isocyanate (1) | 35.2 |
| Pigment paste (2) | 7.5 |
| Dibutyltin dilaurate | 0.6 |
| Ethylene glycol monoethyl acetate | 12.2 |
| Acetone | 8.2 |

(1) The isocyanate is an isophorone diisocyanate-based isocyanurate-containing adduct available from the Thorson Chemical Co. as T-1890.
(2) The pigment paste contains 46.2 percent aluminum; 25.0 percent of a pigment grind resin based on 10 percent hydroxyethyl acrylate, 2.5 percent methacrylic acid (with 25 percent of the methacrylic acid reacted with hydroxy ethyl ethyleneimine), 30 percent styrene, 20 percent 2-ethylhexyl acrylate, 19.5 percent butyl methacrylate and 18 percent methyl methacrylate; and 28.8 percent solvent.

The above composition is sprayed onto a metal panel and baked at 80° C. for 25 minutes to give a dry film of 1.4 mils thickness. The resultant coating provides a durable finish as measured by its solvent-resistance and water-resistance. Additionally, the coating's adhesion to the substrate and its appearance are satisfactory.

The above examples illustrate the making of the esters of imidazolidinedione-based triepoxides of the invention and their use in coating compositions.

What is claimed is:

1. An ester of imidazolidinedione-based triepoxide having the formula:

$$\begin{array}{c}
\text{R}' \quad\quad\quad\quad\quad \text{O} \\
| \quad\quad\quad\quad\quad // \\
\text{R}-\text{C}-\!\!\!-\!\!\!-\!\!\!-\text{C} \\
| \quad\quad\quad\quad\quad\quad \\
\text{XO}-\text{CH}_2-\text{CH}-\text{CH}_2-\text{N} \quad\quad \text{N}-\text{CH}_2-\text{CH}- \\
| \quad\quad\quad\quad \diagdown\;\diagup \quad\quad\quad\quad | \\
\text{OX} \quad\quad\quad\quad \text{C} \quad\quad\quad\quad\quad\; \text{O} \\
\quad\quad\quad\quad\quad\;\; \| \quad\quad\quad\quad\quad\;\; | \\
\quad\quad\quad\quad\quad\;\; \text{O} \quad\quad\quad\quad\quad\;\; \text{CH}_2 \\
\quad\quad\quad\quad\quad\quad\quad\quad\quad\quad\quad\quad\quad\text{ZO}-\text{CH} \\
\quad\quad\quad\quad\quad\quad\quad\quad\quad\quad\quad\quad\quad\quad\quad\; | \\
\quad\quad\quad\quad\quad\quad\quad\quad\quad\quad\quad\quad\quad\quad\quad\text{CH}_2 \\
\quad\quad\quad\quad\quad\quad\quad\quad\quad\quad\quad\quad\quad\quad\quad\; | \\
\quad\quad\quad\quad\quad\quad\quad\quad\quad\quad\quad\quad\quad\quad\quad\text{OZ} \\
\quad\; \text{O} \quad\quad\quad\quad \text{R}' \\
\quad\;\; \diagdown\quad\quad\quad\quad | \\
\quad\quad\;\; \text{C}-\!\!\!-\!\!\!-\text{C}-\text{R} \\
\quad\quad\;\; | \quad\quad\quad\quad | \\
-\text{CH}_2-\text{N} \quad\quad \text{N}-\text{CH}_2-\text{CH}-\text{CH}_2-\text{OY} \\
\quad\quad\quad\;\; \diagdown\;\diagup \quad\quad\quad\quad\quad\quad | \\
\quad\quad\quad\quad\; \text{C} \quad\quad\quad\quad\quad\quad\quad\;\; \text{OY} \\
\quad\quad\quad\quad\; \| \\
\quad\quad\quad\quad\; \text{O}
\end{array}$$

wherein R and R' are independently hydrogen or hydrocarbon groups having from 1 to 8 carbons atoms, one X is hydrogen, one Y is hydrogen, one Z is hydrogen and the other X, Y and Z are $$\begin{array}{c} \text{O} \\ \| \\ -\text{C}-\text{R}'' \end{array}$$

where the R" groups are independently hydrocarbon groups having from 1 to 17 carbon atoms.

2. The ester of claim 1 wherein R and R' are hydrogens.

3. The ester of claim 1 wherein R and R' are alkyl groups.

4. The ester of claim 3 wherein the alkyl groups have from 1 to 5 carbon atoms.

5. The ester of claim 4 wherein the R and R' groups are joined to form a cycloalkyl group.

6. The ester of claim 1 wherein R is hydrogen and R' is an alkyl group.

7. The ester of claims 2, 3 or 6 wherein the R" groups are alkyl groups.

8. The ester of claim 7 wherein the R" alkyl groups have from 7 to 17 carbon atoms.

9. The ester of claims 2, 3 or 6 wherein the R" groups are alkenyl groups having from 4 to 17 carbon atoms.

10. The ester of claims 2, 3 or 6 wherein the R" groups are aryl or alkylaryl groups having from 6 to 10 carbons atoms.

* * * * *